US011484199B2

(12) United States Patent
Chiang (10) Patent No.: US 11,484,199 B2
(45) Date of Patent: Nov. 1, 2022

(54) SYSTEM AND METHOD FOR PREDICTING A BLOOD GLUCOSE LEVEL OF A USER

(71) Applicant: Bryan Hau-Ping Chiang, San Jose, CA (US)

(72) Inventor: Bryan Hau-Ping Chiang, San Jose, CA (US)

( * ) Notice: Subject to any disclaimer, the term of this patent is extended or adjusted under 35 U.S.C. 154(b) by 507 days.

(21) Appl. No.: 16/743,596

(22) Filed: Jan. 15, 2020

(65) Prior Publication Data

US 2020/0305709 A1    Oct. 1, 2020

Related U.S. Application Data

(60) Provisional application No. 62/827,817, filed on Apr. 1, 2019.

(51) Int. Cl.
*G06V 40/18*   (2022.01)
*A61B 3/12*    (2006.01)
*G06T 7/00*    (2017.01)
*A61B 5/145*   (2006.01)

(52) U.S. Cl.
CPC ........ *A61B 3/1216* (2013.01); *A61B 5/14532* (2013.01); *G06T 7/0012* (2013.01); *G06T 2207/20084* (2013.01)

(58) Field of Classification Search
CPC ... A61B 3/1216; A61B 5/14532; A61B 5/163; A61B 5/7267; A61B 3/0025; A61B 3/14; G06T 7/0012; G06T 2207/20084; G06T 2207/20081; G06T 2207/30041; G06N 3/08; G06N 5/003; G06N 20/00; G06N 3/0454
See application file for complete search history.

(56) References Cited

U.S. PATENT DOCUMENTS

2016/0058279 A1* 3/2016 Torres ................... A61B 3/14
                                                351/246
2016/0292159 A1* 10/2016 Patel ................... G06F 16/95
2019/0191995 A1* 6/2019 Giovinazzo ............ A61B 3/112

* cited by examiner

*Primary Examiner* — Chuong A Ngo
(74) *Attorney, Agent, or Firm* — Burris Law, PLLC (57) ABSTRACT

A method of predicting a blood glucose level of a user, comprising: obtaining, by an image capturing device, an iris image of the user; training a first convolutional neural network of a computing device using the iris image as an input to obtain a classification of the iris image; training a second convolutional neural network of the computing device using the classification and the iris image to extract an iris feature vector; and predicting, by the computing device, the blood glucose level of the user based on the iris feature vector.

18 Claims, 6 Drawing Sheets

SYSTEM AND METHOD FOR PREDICTING A BLOOD GLUCOSE LEVEL OF A USER

CROSS-REFERENCE TO RELATED APPLICATION

This application claims the benefit of U.S. Provisional Application No. 62/827,817, filed Apr. 1, 2019, and titled "A Multistage Deep Transfer Learning Computer Vision Model for Low-Cost, Non-Invasive Blood Glucose Monitoring of Diabetes through Smartphone-based Ophthalmic Imaging," the content of which is incorporated herein by reference in its entirety.

FIELD

The present disclosure relates generally to non-invasive systems and methods for predicting blood glucose levels of patients for diabetes management.

BACKGROUND

The statements in this section merely provide background information related to the present disclosure and may not constitute prior art.

Diabetes mellitus is a medical condition that results in erratic blood sugar levels due to a lack or resistance to insulin in the human body. From 1984 to 2014, the number of people with diabetes worldwide had quadrupled to over 422 million people, with over 30 million living in America. It is the 7th leading cause of death in the US, and there is no cure. Thus, proper diabetes management is crucial to long-term survival. Daily blood glucose monitoring is the foundation of effective diabetes management. Patients plan their diet and physical activity around blood glucose levels to minimize hyperglycemic and hypoglycemic complications, and doctors analyze long-term glucose patterns to track disease progression, optimize insulin therapy, and recommend lifestyle changes for patients.

The two current gold standards are finger-prick tests and continuous glucose monitors (CGMs). Finger-prick testing utilizes glucometers and test strips to analyze blood glucose concentration in blood drops extracted from fingers. CGMs measure blood glucose levels in the interstitial fluid underneath the skin. Unfortunately, both methods are plagued with several key issues that prevent streamlined daily monitoring.

First, invasive methods require lancet pricking of the fingers multiple times a day. This causes significant discomfort and reduces the rate of self-monitoring. Additionally, it becomes hard for children to pick up strong self-monitoring and self-care habits due to the pain involved in the process.

Moreover, a new test strip is used for every finger-prick test, and CGMs require new sensors every week (over $100/sensor). Insurance providers cover CGM and test strip costs only in rare instances on a case-by-case basis. Over time, these costs quickly add up in thousands of extra medical dollars per year, proving to be unsustainable for diabetic patients from low-income or underprivileged backgrounds. On average, health costs for diabetics are 2.3× greater than those without diabetes due to the significant financial burden of self-monitoring.

CGMs also need to be calibrated 2-4 times a day with finger-prick tests, so there is little gain in convenience over traditional finger-prick tests. Additionally, patients need to constantly reorder finger prick tests, replace glucometers, and ensure that the equipment they're using is sanitary. This poses further mental obstacles for patient self-monitoring and increases the opportunity cost of managing and organizing medical supplies.

Finger stick tests involve multiple moving pieces, including test strips, meters, and lancets. For patients constantly on the go for professional or personal purposes, it's difficult to keep track of all the different parts and monitor blood glucose levels on the move. In addition, CGMs can hinder more extreme physical movement and exercise, posing additional difficulties for everyday monitoring.

Finger-prick tests require numerous steps and several few minutes to complete. Patients first need to clean their hands, prick their fingers with a lancet to obtain a drop of blood, place the blood drop on a test strip, and insert the test strip into a meter to obtain the final blood glucose reading. Further, it typically takes up to 20 seconds for results to appear. This dramatically increases the friction for daily monitoring for time-strapped and busy professionals, often resulting in neglect of self-monitoring. For elderly populations, whose health is even more sensitive to blood sugar fluctuations, the number of steps can also pose a significant effort barrier for consistent monitoring and care.

The above-mentioned issues are addressed in the present disclosure.

SUMMARY

In one form, the present disclosure provides a method of predicting a blood glucose level of a user, including: obtaining, by an image capturing device, an eye image of the user; training a first convolutional neural network of a computing device using the eye image as an input to obtain a classification of the eye image; training a second convolutional neural network of the computing device using the classification and the eye image to extract an iris feature vector; and predicting, by the computing device, the blood glucose level of the user based on the iris feature vector.

In another form, a method of predicting a blood glucose level of a user includes: obtaining, by an image capturing device, an eye image of the user; training a first convolutional neural network to classify the eye image as having one of a high glucose level and a low glucose level; applying one or more transformations to the iris image by introducing variations to the eye image to create an augmented dataset; training a second convolutional neural network to extract an iris feature vector from the augmented dataset; training a regression module by using the iris feature vector to obtain a prediction of the blood glucose level.

It should be noted that the features which are set out individually in the following description can be combined with each other in any technically advantageous manner and set out other variations of the present disclosure. The description additionally characterizes and specifies the present disclosure, in particular in connection with the figures.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

In this application, including the definitions below, the term "module" may be replaced with the term "circuit". The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Figure 1:
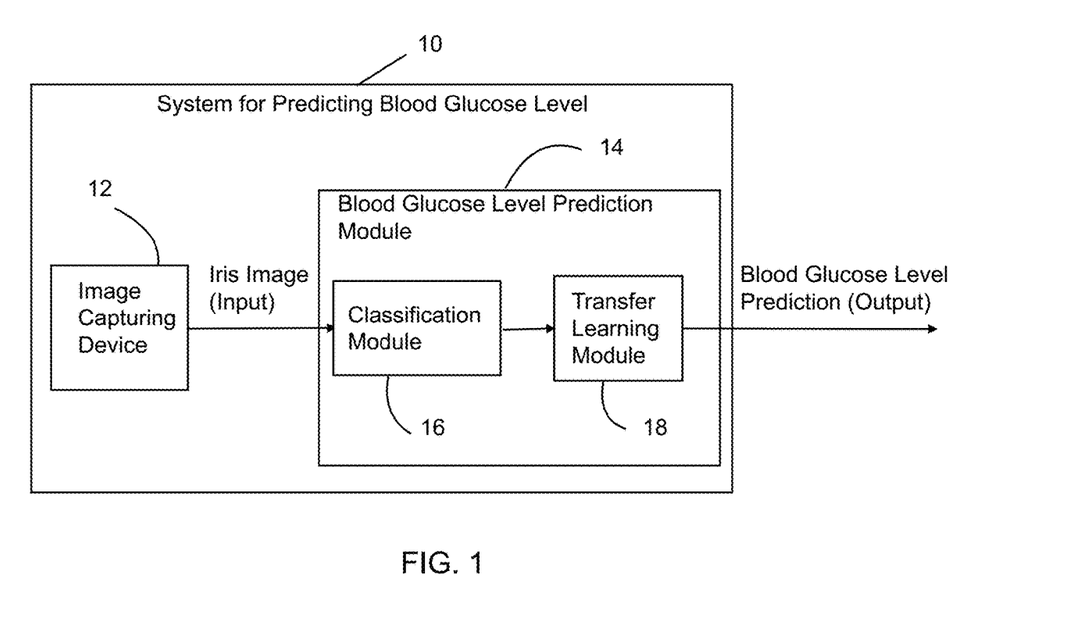
FIG. 1 is a schematic diagram of a system for predicting a blood glucose level constructed in accordance with the teachings of the present disclosure.
Figure 2:
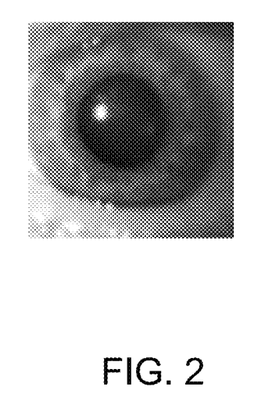
FIG. 2 is a sample iris image for machine learning by a blood glucose level prediction module of FIG. 1.

Referring to FIG. 1, a system 10 for predicting a blood glucose level of a user generally includes an image capturing device 12 for capturing an image of a user's eye (particularly, an iris image) and a blood glucose level prediction module 14 for receiving the iris image as an input and for predicting the blood glucose level of the user based on the iris image. As shown in FIG. 2, the iris image may be a high-resolution image of a diabetic patient's eye.

The blood glucose level prediction module 14 includes a multi-stage computer vision framework for directly predicting a blood glucose level of the user based on the iris image in a non-invasive manner. The blood glucose level prediction module 14 includes a classification module 16 and a transfer learning module 18.

In one form, the glucose level prediction module 14 may be an application integrated in a computing device, such as a laptop computer, a desktop computer, a server, a network computer, a personal digital assistant (PDA), a smart phone, and a tablet. The glucose level prediction module 14 is in communication with the image capturing device 12 and can interface with the image capturing device 12 to obtain eye images, particularly iris images, from a user for end-to-end blood glucose level inference. The image capturing device 12 may be an integral part of the computing device or may be external to the computing device. As an example, the glucose level prediction module 14 may be integrated in a mobile application on smartphone platforms such as iOS or Android, and the image capturing device 12 may be a smartphone-based ophthalmic adapter to be mounted to a smart phone.

The blood glucose level prediction module 14 performs various machine learning and image processing steps and leverages deep transfer learning and extreme gradient boosting machine learning algorithms to directly predict blood glucose levels of the user based on an iris image of a user. The various machine learning and image processing steps are divided into a classification phase and an inference phase, which are performed by the classification module 16 and the transfer learning module 18, respectively.

More specifically, the classification module 16 is configured to receive the iris image of the user from the image capturing device 12 and is trained to classify the iris image. The classification module 16 may include a convolutional neural network (CNN) 19 that is pre-trained using an original set of digital iris images collected from a database to classify the original set of the digital iris images into a plurality of classes based on a predetermined classification. After pre-trained by the original set of digital iris images, the classification module 16 may be used to classify any iris images of the user based on the predetermined classification and the plurality of classes that have been classified by the classification module 16.

In one form, the predetermined classification may include a class of low blood glucose level and a class of high blood glucose level. The high blood glucose level may be set to be any value equal to or above 100 mg/dL, and the low blood glucose level may be set to be any value below 100 mg/dL. The new iris image, which is inputted to the classification module 16 and whose blood glucose level is to be determined, may be classified and labeled as having a low or high glucose level.

It is understood that any other values instead of 100 mg/dL may be used without departing from the scope of the present disclosure. It is also understood that the predetermined classification may include more than two classes, such as a class of low blood glucose level, a class of a medium blood glucose level, and a class of a high blood glucose level without departing from the scope of the present disclosure.

The convolutional neural network 19 of the classification module 16 may be an existing convolutional neural network, such as iTracker, which is pre-trained on the GazeCapture dataset of over 2.5 million iris images originally designed for gaze tracking purposes. The existing convolutional neural network is originally trained to predict a person's gaze based on images of their eyes using the gaze tracking model. The hypothesis is that this "pre-trained" convolutional neural network has already learned image features that are relevant to this human iris. The convolutional neural network was initialized with the weights of iTracker, and then fine-tuned (i.e. trained) through Adam optimization at a low learning rate to differentiate between the low and high glucose level iris images. The fine-tuning of the convolutional neural network may be performed by using a transfer learning approach to create a smaller dataset of digital iris images for each class based on the predetermined. As a result, the original dataset may be divided into a plurality of sub-datasets corresponding to the plurality of classes based on the predetermined classification used by the classification module 16.

Figure 3:
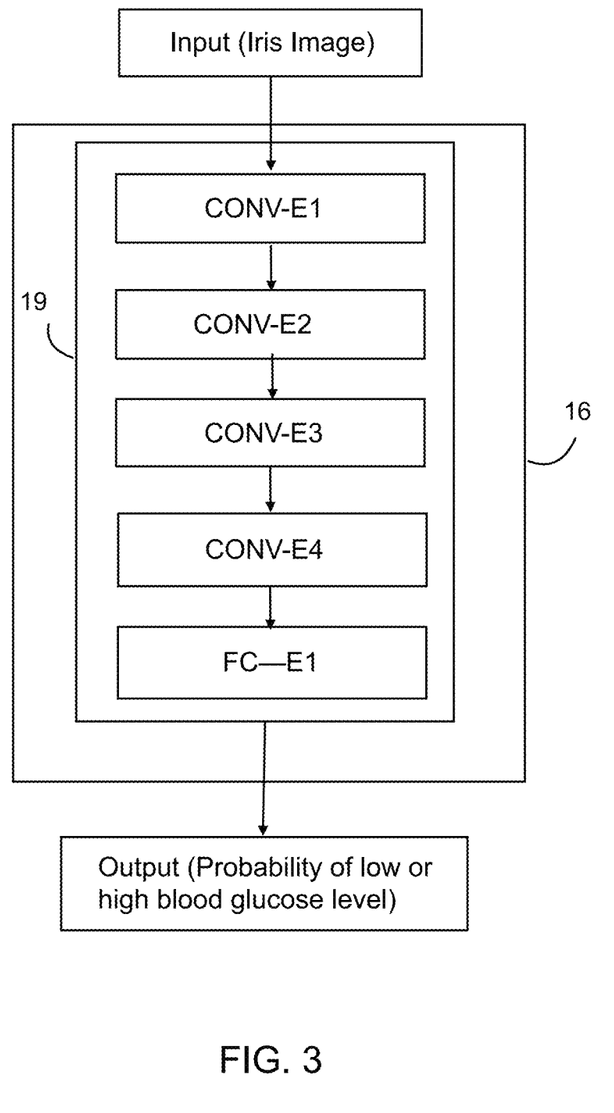
FIG. 3 is schematic diagram of a pre-trained convolutional neural network in a classification module of a blood glucose level prediction module of FIG. 1.

Referring to FIG. 3, an exemplary pre-trained convolutional neural network 19 for transfer learning process in the classification phase is shown. The pre-trained convolutional neural network 19 is configured and trained to perform the classification task, which is the task of learning to approximate a mapping function in which the outputs are discrete labels (i.e. categories). As shown, the pre-trained convolutional neural network 19 includes a plurality of layers CONV-E1, CONV-E2, CONV-E3, CONV-E4, and FC-E1 that are fully connected for processing a series of convolutional operations on the iris images inputted to the classification module 16. The fully connected layer at the end enables a final prediction of the probabilities of the iris image falling into the low or high blood glucose reading range. The iris images and the associated classes determined by the classification module 16 are sent to the transfer learning module 18 for further processing and learning.

Figure 4:
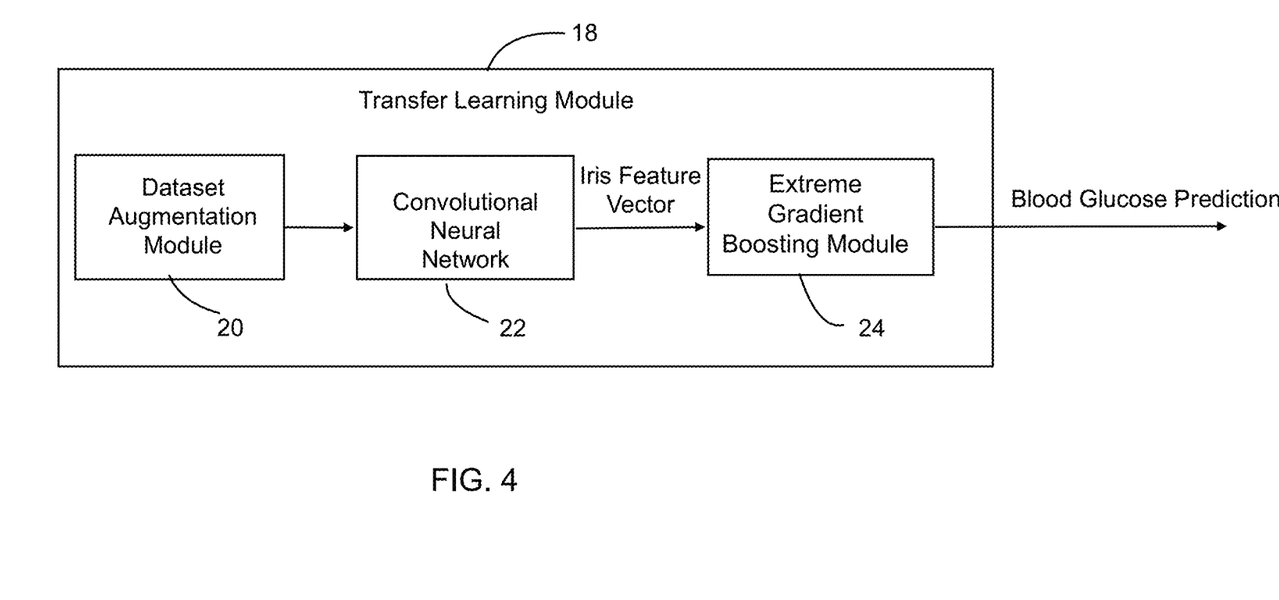
FIG. 4 is a schematic diagram of a transfer learning module of the blood glucose level prediction module of FIG. 1.

Referring to FIG. 4, the transfer learning module 18 is configured to provide an inference for the final blood glucose level prediction based on the iris image and the associated class. The transfer learning module 18 includes a dataset augmentation module 20, a pre-trained convolutional neural network 22, and an extreme gradient boosting module 24.

The dataset augmentation module 20 receives the iris image and the associated class from the classification module 16, and augments the inputted iris image with a variety of image transformations to increase model generalization ability. For diabetic patients, day-to-day usage of the blood glucose monitoring system will likely involve capturing iris images in different lighting conditions, orientations, and angles. To ensure that the blood glucose level prediction module 14 is robust against these variations, the dataset augmentation module 20 is trained to create an artificially augmented dataset. The original dataset of digital iris images may be augmented with image augmentation methods, including but not limited to, crops, rotations, flips, Gaussian blurs, and affine transformations, to create an augmented dataset of digital iris images. The original dataset of digital iris images may be augmented by introducing variations into the original dataset of iris images. For example, the iris image being inputted into the dataset augmentation module 20 may be randomly distorted/rotated/blurred and/or the lighting/contrast of the inputted iris image may be randomly changed to generate an augmented dataset including image transformations. This augmented dataset ensures that the blood glucose level prediction module 14 can accurately predict blood glucose levels with different types of iris images representative of the types of iris images that regular diabetic patients will capture on a daily basis.

As a non-limiting example, both the classification module 16 and the dataset augmentation module 20 of the transfer learning module 18 may rely on a dataset of iris images and corresponding blood glucose levels donated by a male Type 1 diabetic in his mid-40s. The iris images may be captured by any means known in the art. For example, the iris images may be captured with PaxosScope, an FDA-registered, portable smartphone anterior segment imaging adapter, or imaging modality such as low-energy cameras mounted on glasses. The blood glucose readings corresponding to the iris images may be obtained by any means known in the art. For example, a Dexcom G6 continuous glucose monitor (CGM) may be used to passively record the blood glucose levels. The blood glucose readings may also be obtained by finger pricks or direct blood samples. For example, the original dataset may include iris recordings of length between 1 and 1.5 minutes. The set of videos were then split into individual images by frame, at a rate of 30 frames per second. The final processed dataset may contain, for example, around 15,000 iris images and the corresponding blood glucose levels. It is understood that any number of iris images may be used without departing from the scope of the present disclosure.

After the original dataset of iris images is augmented by the dataset augmentation module 20, the convolutional neural network 22 is pre-trained using the augmented dataset of digital iris images as training data. The convolutional neural network 22 may be pre-trained to track gaze in the iris images to extract a linear high-level feature vector from each of the iris images in the augmented dataset. The iris feature vector is a glucose-dependent feature and can be used to provide an indication of the blood glucose level. In one form, the iris feature vector relates to morphological variations of key iris structures such as crypts and furrows.

The convolutional neural network 22 may have an architecture similar to that of the convolutional neural network 19 in the classification module 16. However, the convolutional neural network 22 of the transfer learning module 18, which is pre-trained for gaze tracking, is not directly fine-tuned for the subsequent regression process since convolutional neural networks are not especially well suited for regression tasks. A transfer learning process may be further used by the convolutional neural network 22 to aid the training of the regression model.

Similar to the classification phase, we hypothesize that the convolutional neural network 22 of the transfer learning module 18 has learned the higher-level image features that are specific to the iris and may have predictive value for a patient's blood glucose level. Therefore, the convolutional neural network 22 may be dissected to obtain an output at a specific cross section of the neural network. This output is the iris feature vector that is extracted from every single iris image.

After the iris feature vector is extracted, the iris feature vector is sent to the extreme gradient boosting module 24, which includes a plurality of regression models corresponding to the plurality of classes based on the predetermined classification used in the classification module 16. The extreme gradient boosting module 24 chooses one of the plurality of regression models to perform machine learning regression process to predict the blood glucose level using the iris feature vector.

Regression is the task of learning to approximate a mapping function in which the outputs are continuous values (i.e. quantities). The regression models in the extreme gradient boosting module 24 are directly trained based on these iris feature vectors instead of the image of the entire iris. This would save time in machine learning since the regression model does not need to learn which iris features are most informative of blood glucose levels. Instead, the relevant features (that are self-learned by the convolutional neural network 22, not chosen by humans) have already been learned by the pre-trained gaze tracking model and can be used directly as input.

In the exemplary embodiment, two distinct regression models for low and high glucose level iris images are included, each regression model can output the final blood glucose level prediction depending on the class determined by the classification module 16. It is understood that more than two distinct regression models may be used depending on the classification used in the classification module 16. Each of the regression models may include the same architecture but is trained on distinct subsets of the entire dataset.

Figure 5:
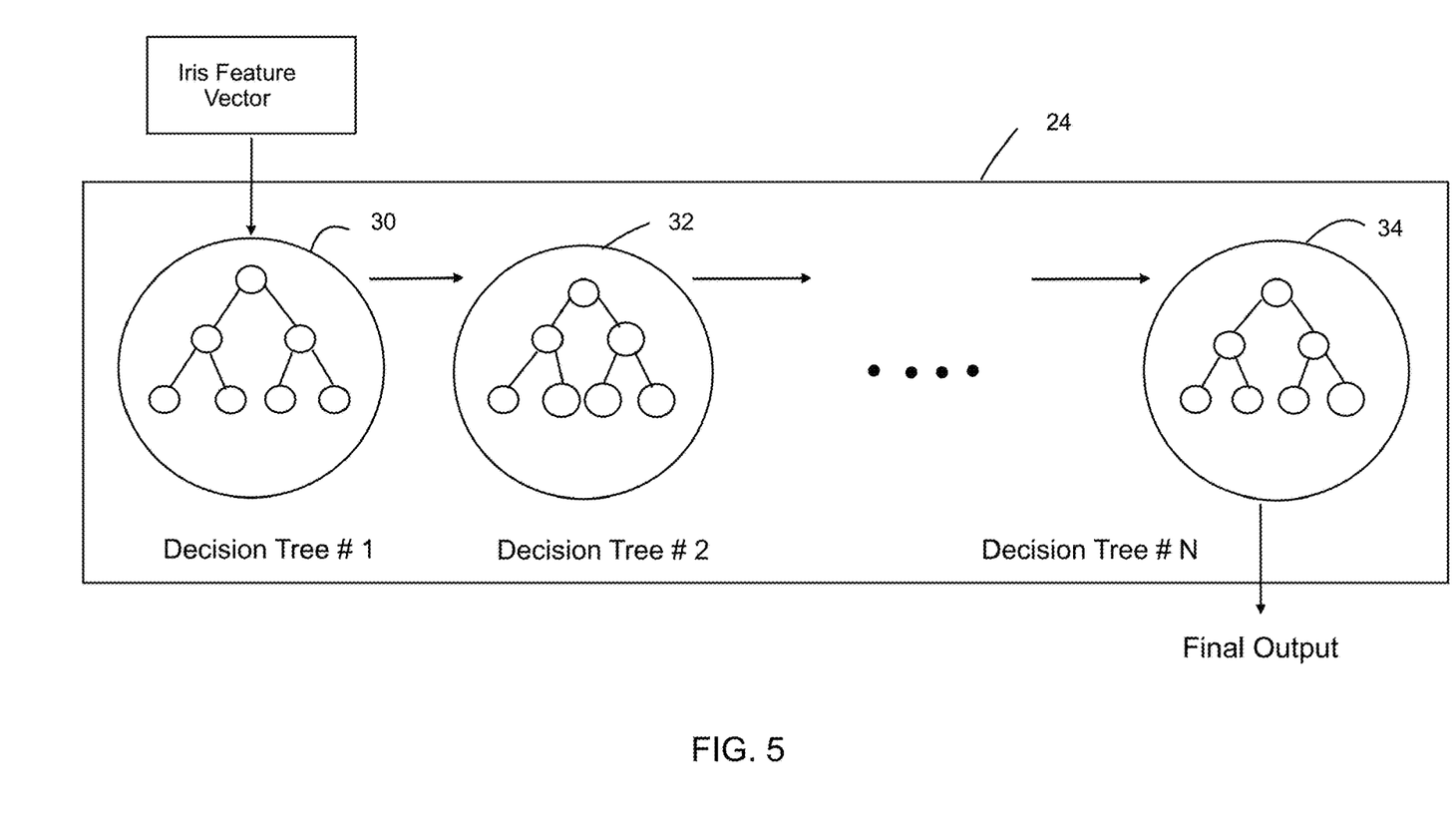
FIG. 5 is a schematic diagram of a regression model of the extreme gradient boosting module of the transfer learning module of FIG. 4.

Referring to FIG. 5, an exemplary regression model is shown to be in the form of extreme gradient boosting trees. Extreme gradient boosting refers to extreme gradient boosted decision trees, which is a specific type of computational model that can be used to perform the regression task.

As shown, the regression model includes a series of N decision trees 30, 32, 34. Decision trees 30, 32, 34 utilize a series of binary (i.e. yes/no) questions to map an input function and output function. At the initial step of gradient boosting, there is a single decision tree named the "base learner". The decision tree is fit to the data to predict the output mapping (i.e. the blood glucose level). In the next steps of gradient boosting, consecutive decision trees are trained in a sequential manner, specifically tailored to fit the mistakes of the previous decision tree. The predictions of the final decision tree are then used as the ultimate prediction of the gradient boosting model.

The average test Mean Absolute Percentage Error (MAPE) for the low glucose level regression model was 7.14%, and the average test MAPE of the high glucose level regression model was 6.72%. The overall average MAPE was 6.93% on a 95% confidence interval with a margin of error of 1.91%. The confidence interval was calculated to prevent bias towards any specifically selected test set.

Figure 6:
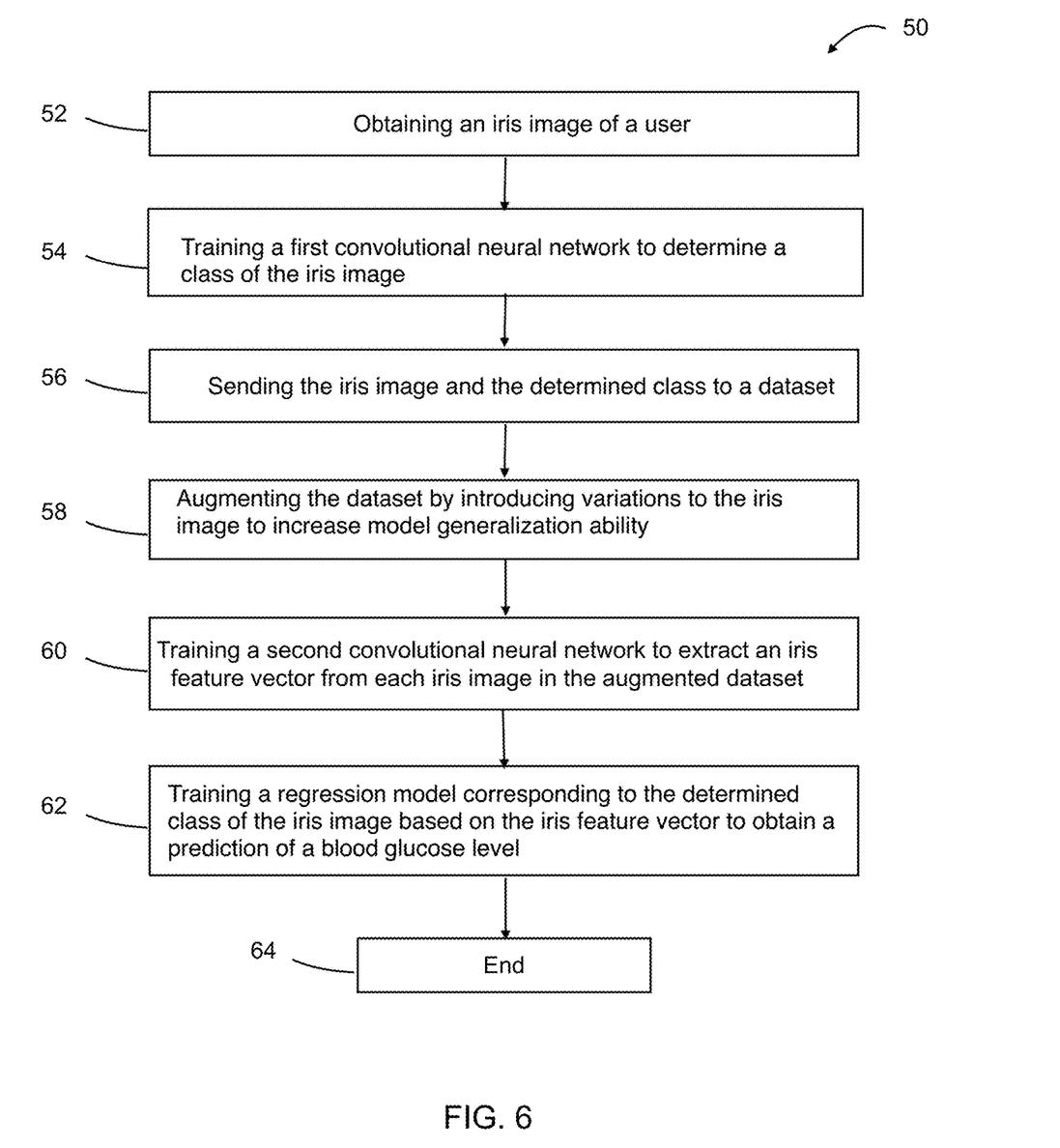
FIG. 6 is a flowchart of a method of predicting a blood glucose level in accordance with the teachings of the present disclosure.

Referring to FIG. 6, a method 50 of predicting a blood glucose level of a user starts with obtaining an eye image, particularly an iris image, by an image capturing device in step 52. The iris image is sent to a classification module 16 in which a first convolutional neural network is trained using the iris image to obtain a class of the iris image (i.e., having a high or low blood glucose level) based on a predetermined classification in step 54. (The first convolutional neural network of the classification module 16 is pre-trained using an original dataset of digital iris images collected from a database.) The iris image together with the class are sent to a dataset in the transfer learning module 18 in step 56. The dataset is an augmented dataset which includes the original dataset of digital iris images and a modified set of digital iris images created by introducing variations to each of the iris images in the original dataset to increase model generalization ability in step 58. The image augmentation methods may include crops, flips, Gaussian blurs, and affine transformations. A pre-trained second convolutional neural network 22 is trained using the augmented dataset to extract a linear high-level feature vector from each of the iris images in the augmented dataset in step 60. The linear high-level feature vector is sent to an extreme gradient boosting module 24 where a regression model corresponding to the class of the iris image inputted to the blood glucose level prediction module is trained using the iris feature vector to obtain a prediction of the blood glucose level in step 62. Both regression models are repeatedly tested against a selected portion of the original dataset unseen during their training phases. The method ends in step 64.

The blood glucose level prediction module 14 (as shown in FIG. 1) and the method 50 of predicting the blood glucose level (as shown in FIG. 6) in accordance with the teachings of the present disclosure use trained regression models and pre-trained convolutional neural networks 19, 22 to predict the blood glucose level of a user based on an inputted iris image. Through transfer learning, the module 14 (FIG. 1) and the method 50 (FIG. 6) of the present disclosure is able to exploit the existing iris specific knowledge and higher-level image feature combinations inside the pre-trained weights to accurately separate low and high glucose level iris images. Following the training process, the fine-tuned convolutional neural network is evaluated against a new, unseen test set to have an accuracy of 98.4%.

Figure 7A:
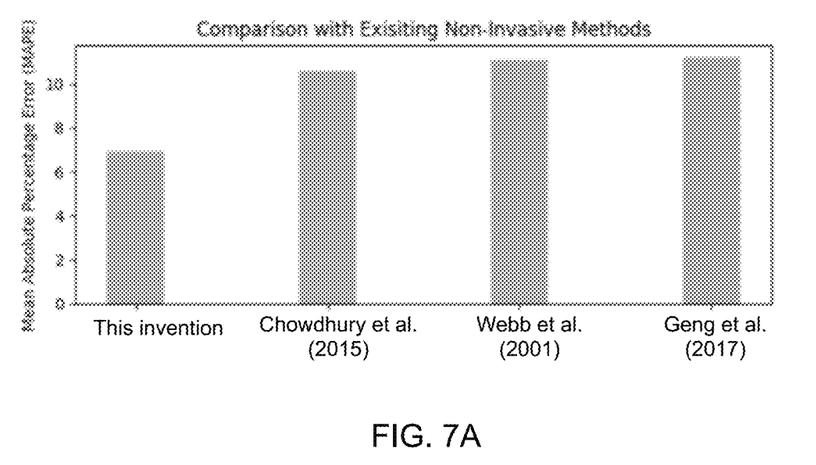
FIG. 7A is a bar chart illustrating an average test Mean Absolute Percentage Error (MAPE) of the system and method of the present disclosure and other existing methods.

Referring to FIG. 7A, a bar graph, which compares the accuracy of the system 10 and method 50 of the present disclosure with existing non-invasive blood glucose monitoring methods, is shown. The existing non-invasive blood glucose monitoring methods being compared in the bar graph includes Chowdhury et. al (2015), Webb et. al (2011), and Geng et al. (2017). Chowdhury et. al (2015) developed a custom hardware solution based on near-infrared spectroscopy to predict blood sugar levels. Webb et. al (2011) developed a linear regression model to predict blood glucose levels from images of rabbit eyes; however, the linear nature of the model limits generalization ability and has not been validated against human eye images. Geng. et al (2017) developed a continuous monitoring solution comprised of multiple sensors attached along the arm, which leverage impedance spectroscopy to estimate glucose variation. As shown, the system and method of the present disclosure has a 6.93% Mean Absolute Percentage Error (MAPE). In contrast, the existing non-invasive blood glucose monitoring methods have an MAPE above 10%. The system and method of the present disclosure has a significantly lower error than that of other existing methods and outperforms the existing methods by nearly 40%.

Figure 7B:
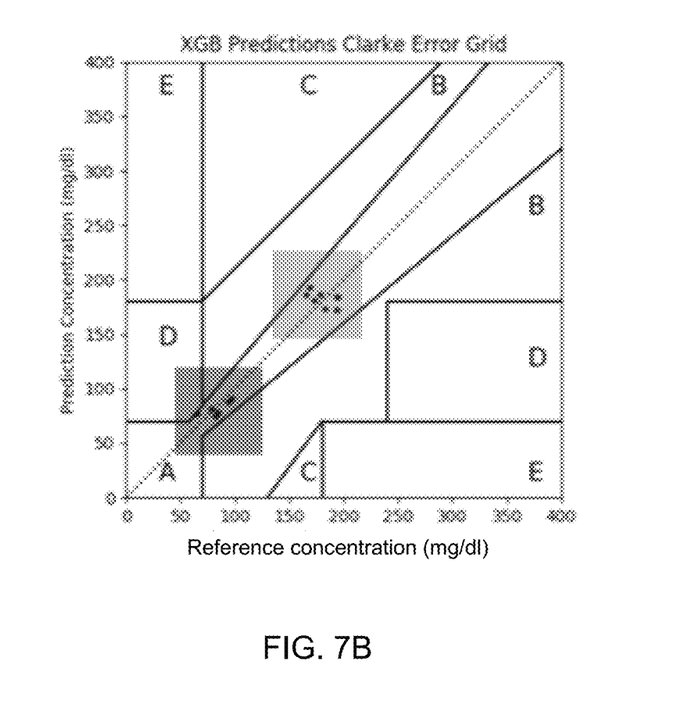
FIG. 7B is a Clarke Error Grid with test predictions by the system and method of the present disclosure plotted against the ground truth reference values.

Referring to FIG. 7B, the test predictions by the system 10 and method 50 of the present disclosure are plotted against the ground truth reference values on the Clark Error Grid Analysis. Clarke Error Grid is one of the "gold standards" for determining accuracy of blood glucose meters as compared to a reference value. As shown, all of the test predictions fall within Zone A, which is the highest possible evaluation on the Clarke Error Grid with an interpretation of "clinically accurate."

The system 10 and method 50 of the present disclosure includes a multi-stage deep transfer learning computer vision framework to provide direct prediction of blood glucose levels based on high-resolution human eye images. This enables painless, cost-effective, non-invasive, and portable blood sugar monitoring for diabetic patients. High-resolution images of the human eye may be first captured with a smartphone-based ophthalmic adapter. Transfer learning convolutional neural networks and extreme gradient boosting trees are then leveraged to analyze morphological variation in iris structures to predict blood glucose levels at an unprecedented Mean Average Percent Error (MAPE) of 6.93%, significantly outperforming current state-of-the-art methods by nearly 40%. The computer vision framework can be integrated into a mobile app on a smartphone platform for end-to-end blood glucose prediction. Iris images can be obtained through developed portable anterior segment imaging adaptors that can be fitted over existing smartphone camera CMOS systems. Day-to-day platform usage requires no long-term maintenance, and the deep learning analysis relies solely on on-device inference without need for an Internet connection.

The systems and methods of the preferred embodiment and variations thereof can be embodied and/or implemented at least in part as a machine configured to receive a computer-readable medium storing computer-readable instructions. The computer-readable medium can be stored on any suitable computer-readable media such as RAMs, ROMs, flash memory, EEPROMs, optical devices (e.g., CD or DVD), hard drives, floppy drives, cloud, or any suitable device. The computer-executable component is preferably a general or application-specific processor, but any suitable dedicated hardware or hardware/firmware combination can alternatively or additionally execute the instructions.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A method of predicting a blood glucose level of a user, comprising:
   obtaining, by an image capturing device, an eye image of the user;
   training a first convolutional neural network of a computing device using the eye image as an input to determine a class of the eye image based on a predetermined classification;
   training a second convolutional neural network of the computing device using the eye image and the class of the eye image to extract an iris feature vector; and
   predicting, by the computing device, the blood glucose level of the user based on the iris feature vector.

2. The method according to claim 1, further comprising collecting an original dataset of digital eye images from a database, and pre-training the first convolutional neural network to classify the original dataset of the digital eye images based on the predetermined classification.

3. The method according to claim 2, further comprising generating a plurality of subsets of digital eye images corresponding to a plurality of classes based on the predetermined classification.

4. The method according to claim 3, wherein the plurality of classes comprise a class of low blood glucose level and a class of high blood glucose level.

5. The method according to claim 4, wherein the eye image is classified by the first convolutional neural network as having one of a low blood glucose level and a high blood glucose level.

6. The method according to claim 3, wherein the computing device comprises a plurality of regression models corresponding to the plurality of classes.

7. The method according to claim 6, further comprising selecting one of the plurality of regression models corresponding to the class of the eye image and training the one of the regression models using one of the plurality of subsets of digital eye images corresponding to the class of the eye image to obtain a prediction of the blood glucose level based on the iris feature vector.

8. The method according to claim 1, wherein the computing device includes a regression model, and the method further comprising training the regression model to obtain a prediction of the blood glucose level by using the iris feature vector.

9. The method according to claim 1, further comprising applying one or more transformations to the eye image to generate an augmented dataset.

10. The method according to claim 9, wherein the transformations include distorting, rotating, blurring, and contrast reduction.

11. The method according to claim 9, wherein the training of the second convolutional neural network is performed based on the augmented dataset.

12. The method according to claim 1, wherein the image capturing device comprises a smartphone-based ophthalmic adapter.

13. The method according to claim 1, wherein the computing device is one selected from a group consisting of a smart phone, a tablet, a desktop computer, a laptop computer, a server, and a personal digital assistant.

14. The method according to claim 1, wherein the eye image is an iris image.

15. The method according to claim 1, wherein the iris feature vector relates to morphological variation of iris structures.

16. A non-transitory computer-readable storage medium having instructions stored thereon that are executable by a processing system of the computing device to perform the method of claim 1.

17. The non-transitory computer-readable storage medium according to claim 16, wherein the medium is one selected from a group consisting of a smart phone, a tablet, a desktop computer, a laptop computer, a server, a personal digital assistant.

18. A method of predicting a blood glucose level of a user, comprising:
   obtaining, by an image capturing device, an iris image of the user;
   training a first convolutional neural network to classify the iris image as having one of a high glucose level and a low glucose level;
   applying one or more transformations to the iris image by introducing variations to the iris image to create an augmented dataset;
   training a second convolutional neural network to extract an iris feature vector from the augmented dataset; and
   training a regression module by using the iris feature vector to obtain a prediction of the blood glucose level.

* * * * *